United States Patent [19]

Azuma et al.

[11] Patent Number: 4,685,952
[45] Date of Patent: Aug. 11, 1987

[54] BENZOYLAMINOALKYLENEPHOSPHONIC ACIDS OR ESTERS THEREOF, HERBICIDAL COMPOSITIONS CONTAINING SAME AND THEIR HERBICIDAL USE

[75] Inventors: Shizuo Azuma; Toshiyuki Hiramatsu; Koji Nakagawa, all of Iwakuni; Yataro Ichikawa, Tokorozawa, all of Japan

[73] Assignee: Teijin Limited, Osaka, Japan

[21] Appl. No.: 848,117

[22] Filed: Apr. 4, 1986

[30] Foreign Application Priority Data

Feb. 7, 1986 [JP] Japan .................. 61-24150

[51] Int. Cl.$^4$ ............ A01N 57/06; A01N 43/06; C07F 9/58; C07F 9/40
[52] U.S. Cl. ...................... 71/86; 546/24; 558/168; 71/94
[58] Field of Search ........ 546/24; 558/168; 71/94, 71/86

[56] References Cited

U.S. PATENT DOCUMENTS

| | | | |
|---|---|---|---|
| 3,683,080 | 8/1972 | Francis | 514/107 |
| 3,941,772 | 3/1976 | Ploger et al. | 546/6 |
| 3,960,888 | 6/1976 | Ploger et al. | 548/412 |
| 3,988,443 | 10/1976 | Ploger et al. | 514/79 |
| 4,034,086 | 7/1977 | Ploger et al. | 514/91 |
| 4,086,334 | 4/1978 | Schmidt-Dunker et al. | 514/11 |
| 4,104,366 | 8/1978 | Schmidt-Dunker et al. | 424/1.1 |
| 4,330,537 | 10/1980 | Francis | 514/105 |
| 4,456,464 | 6/1984 | Lee et al. | 71/87 |
| 4,456,465 | 6/1984 | Lee | 71/87 |
| 4,605,434 | 8/1986 | Maier | 71/94 |

OTHER PUBLICATIONS

Mustafa et al., *Ann.*, 698, 109 (1966).
Gross et al., *Liebigs Ann. Chem.*, 707, 35 (1967).

*Primary Examiner*—Alan L. Rotman
*Attorney, Agent, or Firm*—Wenderoth, Lind & Ponack

[57] ABSTRACT

A benzoylaminoalkylphosphonic acid represented by the following formula (I)

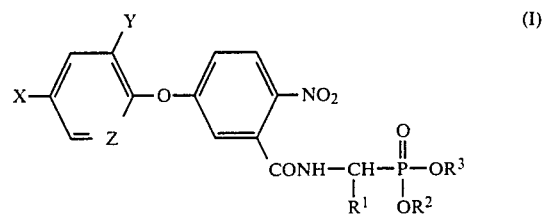

wherein X and Y are identical or different, and each represents a hydrogen atom, a halogen atom, $CF_3$, or an alkyl group having not more than 5 carbon atoms, Z is CH or N, and $R^1$, $R^2$ and $R^3$ are identical or different and each represents a hydrogen atom or a lower alkyl group having 1 to 5 carbon atoms. The compound is useful, as a herbicide, for eradicating weeds, especially broad-leaved weeds.

8 Claims, No Drawings

BENZOYLAMINOALKYLENEPHOSPHONIC ACIDS OR ESTERS THEREOF, HERBICIDAL COMPOSITIONS CONTAINING SAME AND THEIR HERBICIDAL USE

This invention relates to a benzoylaminoalkylphosphonic acid and a herbicide comprising it as an active ingredient. More specifically, this invention pertains to benzoylaminoalkylphosphonic acids which have selective herbicidal activity and selectively eradicate broad-leaved weeds without substantially harming the growth of narrow-leaved crop plants as well as broad-leaved crop plants.

Herbicides of the type which selectively kills broad-leaved weeds, typified by 2,4-dichlorophenoxyacetic acid, are known as selective herbicidally active compounds. The selectivity of the herbicidal activity of 2,4-dichlorophenoxyacetic acid is between narrow-leaved plants including crop plants and weeds and broad-leaved plants including crop plants and weeds. It is known that 2,4-dichlorophenoxyacetic acid has very little or no activity against narrow-leaved plants [see, for example, Nature, Vol. 155, page 498 (1945)]. It is known on the other hand that compounds resulting from introduction of a chloro- or trifluoromethyl-substituted phenoxy group or a chloro- or trifluoromethyl-substituted pyridyloxy group into the aromatic group of the above compound have the activity of selectively killing narrow-leaved plants (see U.S. Pat. Nos. 4270948, 4309562, 4314069, 4332961 and 3954442, British Pat. No. 1,579,201, and Japanese Laid-Open Patent Publications Nos. 125626/1977 and 15825/1977). These compounds, however, also kill useful crops such as rice or corn.

U.S. Pat. No. 3,928,416 discloses that diphenyl ethers represented by the following formula

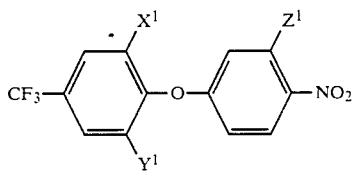

wherein X is a hydrogen atom, a halogen atom, a trihalomethyl, a $C_1$–$C_4$ alkyl or cyano, Y is a hydrogen atom, a halogen atom, or a trihalomethyl, and Z is a hydroxy, an alkoxy, an alkyl, a halogen atom, an amino, a cyano, a carboxy, a carbalkoxy, —$CO_2R$, a carboxyalkyl —R′-$CO_2H$, a carbaloxyalkyl —R′$CO_2R$, an alkanoyloxy —OCOR, a carbamoyloxy, —O—, —$CONH_2$, —O-CONHR or —$OCONR_2$, have herbicidal activity.

European Laid-Open Patent Publication No. 165,203 discloses benzoyloxyalkylphosphonic or phosphinic acids represented by the following formula

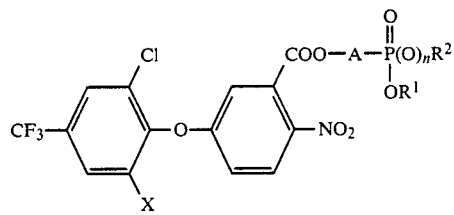

wherein X is H or Cl, n is 0 or 1, A is $C_1$–$C_3$ alkyl substituted by one or two $C_1$–$C_2$ alkyls and/or one or two phenyls, and $R^1$ and $R^2$, independently from each other, represent H or $C_1$–$C_4$ alkyl. Tables 2 to 4 of this patent document show that the above compounds show excellent effects against various weeds but cause unneglible phytotoxicity to the growth of wheat, corn, soybean, cotton or rice.

U.S. Pat. No. 4,364,767 discloses herbicidal compounds of the following formula

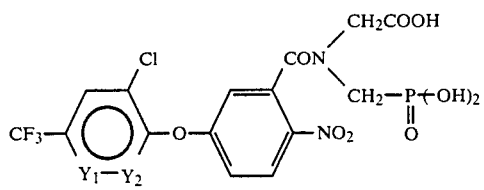

wherein $Y_1$ is N or CH, $Y_2$ is N or CH provided that $Y_1$ is not N when $Y_2$ is CH, and agronomically acceptable salts thereof. This U.S. Patent discloses no data showing the herbicidal activity of the above compounds.

U.S. Pat. No. 4,536,355 discloses a herbicide represented by the following formula

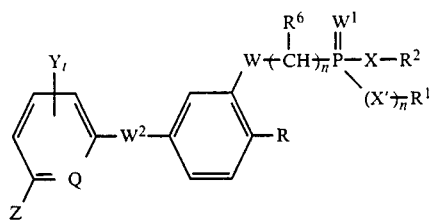

wherein R is, for example, nitro, n is 0 or 1, n′ is 1, 2 or 3, $R^1$ is, for example, hydrogen, or lower alkyl, $R^2$ is, for example, hydrogen or lower alkyl, $R^6$ is, for example, hydrogen, or lower alkyl, Q is CH or N, W is oxygen, sulfur, sulfinyl, sulfonyl or $NR^5$ in which $R^5$ is hydrogen or lower alkyl, $W^1$ is oxygen or sulfur, $W^2$ is, for example, oxygen, each of X and X′ is, for example, oxygen, each of Y and Z is, independently, hydrogen, lower alkyl, lower haloalkyl, halogen, lower alkoxy, lower haloalkoxy, cyano or nitro, and t is 1 or 2.

It is an object of this invention to provide a novel benzoylaminoalkylphosphonic acid.

Another object of this invention is to provide a selective herbicide showing selective herbicidal activity.

Another object of this invention is to provide a selective herbicide which selectively kills broad-leaved weeds without substantially inhibiting the growth of narrow-leaved plants and substantially affecting broad-leaved useful plants.

Another object of this invention is to provide a selective compound which eradicates narrow-leaved and broad-leaved weeds without substantially causing phytotoxicity to useful crops, for example broad-leaved crops such as soybean, cotton, sunflower and beet and narrow-leaved crops such as rice, corn and wheat, and therefore without substantially inhibiting the growth of these useful crops; and a herbicide containing the above compound.

Another object of this invention is to provide a compound which kills many broad-leaved and narrow-leaved plants or inhibits their growth without causing substantial phytotoxicity to narrow-leaved crops such as rice, corn and wheat and various broad-leaved crops, and therefore when applied to a locus where the aforesaid useful crops and hazardous weeds grow together, can create a condition in which the useful crops easily grow beyond the growth of the weeds.

Another object of this invention is to provide a selective herbicide applicable by foliar spraying and soil treatment, which can kill, or inhibit the growth of, weeds by application to their foliage, and also can inhibit the emergence of weeds without substantially inhibiting the emergence of useful crops by application to the soil before emergence.

Another object of this invention is to provide a selective herbicide which has low toxicity to animals and fish and remains little in the soil.

Another object of this invention is to provide a method of eradicating weeds by using the aforesaid compounds or herbicides of this invention.

Further objects of this invention along with its advantages will become apparent from the following description.

According to this invention, the objects and advantages of this invention are achieved by a benzoylaminoalkylphosphonic acid represented by the following formula (I)

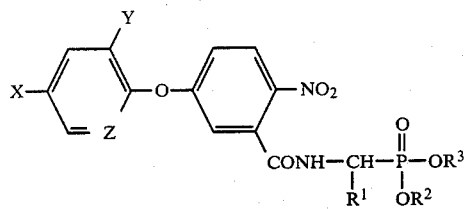
(I)

wherein X and Y are identical or different, and each represents a hydrogen atom, a halogen atom, $CF_3$, or an alkyl group having not more than 5 carbon atoms, Z is CH or N, and $R^1$, $R^2$ and $R^3$ are identical or different and each represents a hydrogen atom or a lower alkyl group having 1 to 5 carbon atoms.

In formula (I), X and Y are identical or different, and each represents a hydrogen atom, a halogen atom, $CF_3$ or an alkyl group having not more than 5 carbon atoms. The halogen atom is, for example, fluorine, chlorine or bromine. The alkyl group having not more than 5 carbon atoms may be linear or branched, and includes, for example, methyl, ethyl, n-propyl, iso-propyl, n-butyl, sec-butyl, iso-butyl, t-butyl and n-pentyl.

In formula (I), at least one of X and Y is preferably a halogen atom, $CF_3$ or an alkyl group having not more than 5 carbon atoms.

Z is CH or N, and the compounds of formula (I) may be divided into the following groups according to the definition of Z for the sake of convenience.

Compounds of formula (I) in which Z is CH are represented by the following formula

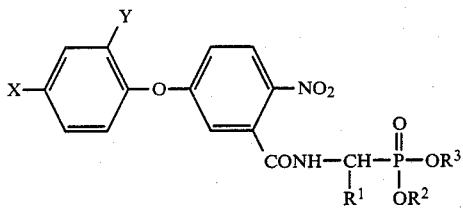
(I)-A wherein X, Y, $R^1$, $R^2$, $R^3$ and $R^4$ are as defined above.

Compounds of formula (I) in which Z is N are represented by the following formula (I)-B

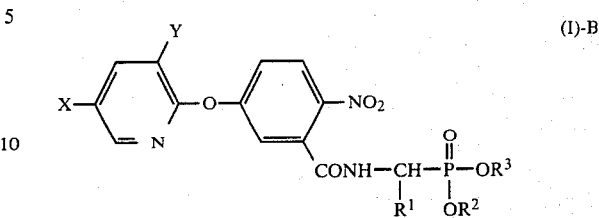
(I)-B wherein X, Y, $R^1$, $R^2$ and $R^3$ are as defined above.

In formula (I) [including formulae (I)-A and (I)-B throughout the specification], $R^1$, $R^2$ and $R^3$ are identical or different and each represents a hydrogen atom or a lower alkyl group having 1 to 5 carbon atoms. Specific examples of the lower alkyl group having 1 to 5 carbon atoms are the same as those given above for X and Y.

$R^1$ is preferably a hydrogen atom or a methyl group. $R^2$ and $R^3$ are preferably a methyl, ethyl, propyl or butyl group.

Examples of the benzoylaminoalkylphosphonic acids of formula (I) are given below.

Compounds of formula (I)-A (100) 2-nitro-5-(2-chloro-4-trifluoromethylphenoxy)-benzoylaminomethyl phosphonic acid diethyl ester,
(102) 2-nitro-5-(2-chloro-4-trifluoromethylphenoxy)-benzoylaminomethyl phosphonic acid di-n-butyl ester,
(104) 2-nitro-5-(4-trifluoromethylphenoxy)benzoylaminomethyl phosphonic acid diethyl ester,
(106) 2-nitro-5-(4-trifluoromethylphenoxy)benzoylaminomethyl phosphonic acid di-n-butyl ester,
(108) 2-nitro-5-(2-chloro-4-trifluoromethylphenoxy)-benzoyl-1-aminoethyl phosphonic acid diethyl ester,
(110) 2-nitro-5-(2-chloro-4-trifluoromethylphenoxy)-benzoyl-1-aminopropyl phosphonic acid diethyl ester.

Compounds of formula (I)-B (200) 2-nitro-5-(3-chloro-5-trifluoromethylpyridine-2-yloxy)benzoylaminomethyl phosphonic acid diethyl ester.
(202) 2-nitro-5-(3-chloro-5-trifluoromethylpyridine-2-yloxy)benzoylaminomethyl phosphonic acid di-n-butyl ester.
(204) 2-nitro-5-(5-trifluoromethyl-pyridine-2-yloxy)-benzoylaminomethyl phosphonic acid diethyl ester.
(206) 2-nitro-5-(5-trifluoromethyl-pyridine-2-yloxy)-benzoylaminomethyl phosphonic acid di-n-butyl ester.
(208) 2-nitro-5-(3-chloro-5-trifluoromethylpyridine-2-yloxy)benzoyl-1-aminoethyl phosphonic acid diethyl ester.
(210) 2-nitro-5-(3-chloro-5-trifluoromethylpyridine-2-yloxy)benzoyl-1-aminopropyl phosphonic acid diethyl ester.

The compound of formula (I) can be produced, for example, by a process shown by the following reaction scheme.

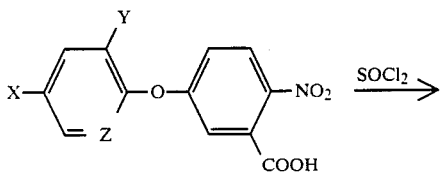

(II)

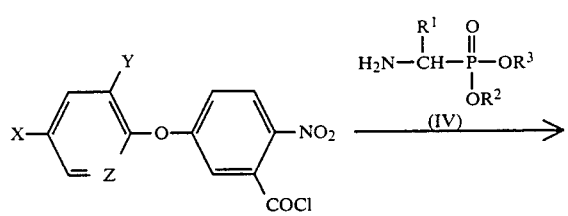

(III)

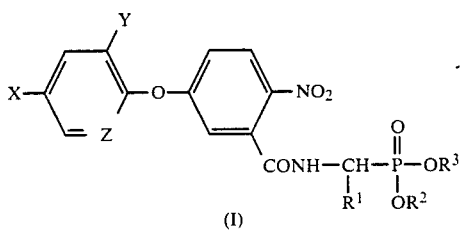

(I)

In formulae (II), (III) and (I), X, Y and Z are as defined above. In formulae (IV) and (I), the definitions of $R^1$, $R^2$ and $R^3$ are the same as given above. The individual steps of the above process are carried out by methods known per se.

When it is desired to obtain a compound of formula (I) in which $R^2$ and $R^3$ are hydrogen atoms by the above process, the above reaction is carried out by using a compound of formula (IV) in which $R^2$ and $R^3$ are hydrogen atoms; or the reaction is carried out by using a compound of formula (IV) in which $R^2$ and $R^3$ are alkyl groups having 1 to 5 carbon atoms to give a compound of formula (I) in which $R^2$ and $R^3$ are the corresponding lower alkyl groups, and the resulting compound (I) is hydrolyzed.

The compounds of formula (I) provided by this invention show selective herbicidal activity, and particularly have the marked property of selectively killing broad-leaved weeds without substantially inhibiting the growth of narrow-leaved plants and substantially affecting useful broad-leaved plants.

Accordingly, the present invention also provides a herbicide comprising the benzoylaminoalkylphosphonic acid of formula (I) as a herbicidally active ingredient.

The compounds of formula (I) provided by this invention can also be applied to seeds of plants, and to plants in various growth stages through foliage or roots. In other words, the compounds of this invention, either as such or as a composition, are applied to plants whose growth is to be inhibited, namely plants whose metabolism is to be regulated, seeds of such plants, a locus where such plants are growing, or a locus where the growth of such plants is anticipated, in amounts sufficient to regulate the metabolism of the plants.

The metabolism of plants can be regulated by applying the compounds of this invention at a rate of 1 g to 2 kg, preferably 5 g to 1 kg, especially preferably 10 g to 200 g, per 10 acres.

When it is desired to inhibit the growth of, or eradicate, hazardous plants by the compounds of this invention, the compounds, either as such or as a composition, can be applied directly to the plants or their seeds or to the soil in amounts sufficient to inhibit the growth of, or eradicate, the plants in a locus where beneficial plants or their seeds and the hazardous plants or their seeds are growing together or are likely to grow together.

The hazardous plants may be defined as plants which come into an environment created by man, such as a paddy or an upland farm, from the surrounding nature, and grow there and which are considered by man to be useless in that environment or do harm to it. Such hazardous plants are generally called weeds. Examples of the weeds to which the compounds of this invention are to be applied are shown below.

Amaranthaceae
  *Amaranthus retroflexas L.*, and
  *Amaranthus lividus Loise I.*
Convolvulaceae
  *Ipomoea purpurea,* and
  *Cuscuta japonica Choisy.*
Polygonaceae
  *Polygonum convolvulus L.,*
  *Polygonum hydropiper L.,* and
  *Polygonum lapathifolium L.*
Chenopodiaceae
  *Chenopodium album L.,*
  *Chenopodium album L. var. centrorubrum Makino,* and
  *Chenopodium ficifolium Smith.*
Portulacaceae
  *Portulaca oleracea L.*
Leguminosae
  *Desmodium tortuosum.*
Malvaceae
  *Abutilon theophrasti,* and
  *Sida spinosa.*
Solanaceae
  *Solanum nigrum L.,* and
  *Datula stramonium L.*
Compositae
  *Erigeron annuus L.,*
  *Ambrosia artemisiaefolia L. var. elator Desc.,*
  *Xanthiu, strumarium L.,* and
  *Cirsium arvense var. etosum.*
Gramineae
  *Sorghum halepense,*
  *Avena fatua,*
  *Digitaria adscendens Henr.,*
  *Setaria faeri,*
  *Agropyron repens,*
  *Pacinum texanum,*
  *Echinochloa crus-galli,*
  *Setaria viridis,*
  *Poa annua,*
  *Eleusine indica,*
  *Axonopus affinis,*
  *Bachiaria platyphylla,*
  *Bromus tectorum,*
  *Cynodon dactylon,*
  *Panicum dichotomiflorum,*
  *Paspalum dilatatum,*
  *Echinochloa colona,*
  *Panicum capillare,* and
  *Setaria lutescens.*

The beneficial plants in the above case are, for example, plants producing cereals, and lawns. Since the compound of this invention exert little or no adverse effect on the growth of not only various narrow-leaved plants such as rice, corn and wheat but also broad-leaved plants such as soybean and cotton, they are very suitable for application to paddies and upland farms for cultivating these plants. By applying the compounds of this invention to a locus where lawns are growing, the emergence and growth of weeds can be inhibited.

In some cases, it is desirable to apply the compounds of this invention while hazardous plants do not grow so much, particularly while the height of the hazardous plants is lower, or a little bit higher, than the height of beneficial plants.

When weeds are to be eradicated by using the compounds of this invention, the compounds can be applied either as such or as a composition to weeds to be eradicated, their seeds, or a locus where such weeds are growing, or are likely to grow, for example in a crop cultivating area, in amounts sufficient for eradication.

The herbicide of this invention shows a very good effect against broad-leaved weeds and also exhibits herbicidal activity against narrow-leaved weeds. When used in dosages which exhibit this effect, the herbicide does not substantially injure the aforesaid useful crops.

Among the compounds of formula (I) provided by this invention, preferred compounds having especially superior selective herbicidal activity are represented by the following formula (I)-1

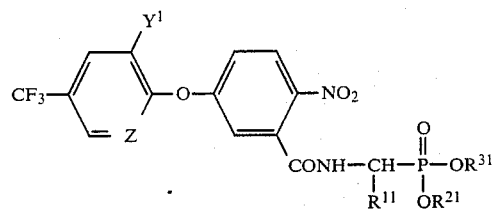

wherein Z is as defined above, $Y^1$ represents H or Cl, $R^{11}$ represents H or $CH_3$, and $R^{21}$ and $R^{31}$ are identical or different and each represents an alkyl group having 1 to 4 carbon atoms.

The compounds of this invention can be used in usual formulations such as a solution, an emulsifiable concentrate, a suspension, a dust, a paste or granules.

Such formulations are prepared by using at least one agriculturally acceptable diluent. Examples include solid carriers such as talc, bentonite, clay, kaolin, diatomaceous earth, white carbon, vermiculite, slaked lime, ammonium sulfate and urea; liquid carriers such as water, alcohols, dioxane, acetone, xylene, cyclohexane, methylnaphthalene, dimethylformamide, N-methylpyrolidone, dimethyl sulfoxide, cyclohexanone, methyl ethyl ketone and methyl isobutyl ketone; surface-active agents, emulsifiers or dispersants such as alkylsulfuric acid esters, alkylsulfonic acid salts, ligninsulfonic acid salts, polyoxyethylene glycol ethers, polyoxyethylene alkylaryl ethers, polyoxyethylene sorbitan monoalkylates and dinaphthylmethanedisulfonic acid salts; and various adjuvants such as carboxylmethyl cellulose and gum arabic.

For example, such a formulation can be prepared by mixing the compound of this invention with the aforesaid carrier and/or emulslifier, etc.

The compound of this invention may be present in a proportion of usually 0.01 to 99% by weight, preferably 0.1 to 95% by weight, in the formulation.

The compound of this invention, as such or in admixture with another active compound or as the aforesaid formulation, can be applied to plants by usual methods such as spraying, atomizing, or dusting.

The following examples illustrate the present invention in greater detail.

In these examples, all parts are by weight unless otherwise specified. The herbicidal activity of the active test compounds was evaluated on a scale of 0 to 5 in which 0 means that the plants were as sound as before the application of the active compound and 5 means that the application of the active compound caused the plants to wither and die, and 1, 2, 3 and 4 mean varying degrees of the enfeebled state of the plants between 0 and 5.

PRODUCTION EXAMPLES

EXAMPLE 1

Production of compound (100):

0.3 Part of 2-nitro-5-(2-chloro-4-trifluoromethylphenoxy)benzoic acid and 0.83 part of thionyl chloride for 2 hours. After the reaction, the excess of thionyl chloride was removed under reduced pressure to give 0.31 part of 2-nitro-5-(2-chloro-4-trifluoromethylphenoxy)benzoyl chloride. The resulting benzoyl chloride was added dropwise to a mixture of 0.14 part of diethylaminomethyl phosphonate, 0.095 part of triethylamine and 6 parts by volume of benzene with ice cooling. After the addition, the mixture was stirred at room temperature for 4 hours, and water was added. The mixture was then extracted with benzene, and the extract was washed with a saturated aqueous solution of sodium hydrogen carbonate and water, and dried over anhydrous sodium sulfate. The solvent was removed under reduced pressure to give 0.3 part of the desired compound (100). The IR and NMR spectral data of the compound are shown in Table 1.

EXAMPLES 2–12

In the same way as in Example 1, compounds (102) to (210) having the atoms or groups indicated in Table 1 were synthesized. The IR and NMR spectral data of these compounds are shown in Table 1.

TABLE 1

| Example | Compound No. | X | Y | Z | R¹ | R² | R³ | IR ν(cm⁻¹) | NMR in CDCl₃ δ(ppm) |
|---|---|---|---|---|---|---|---|---|---|
| 1 | (100) | —CF₃ | Cl | =CH— | H | —C₂H₅ | —C₂H₅ | 3250<br>1660<br>1580<br>1320<br>1260<br>1080 | 1.23–1.47(6H)<br>3.73–4.00(2H)<br>3.90–4.40(4H)<br>6.90–8.27(7H) |
| 2 | (102) | —CF₃ | Cl | =CH— | H | —C₄H₉ | —C₄H₉ | 3250<br>1660<br>1580<br>1320<br>1260<br>1080 | 0.77–1.17(6H)<br>1.17–1.93(8H)<br>3.70–3.97(2H)<br>3.90–4.33(4H)<br>6.90–8.30(7H) |
| 3 | (104) | —CF₃ | H | =CH— | H | —C₂H₅ | —C₂H₅ | 3250<br>1660<br>1580<br>1320<br>1240<br>1020 | 1.17–1.40(6H)<br>3.62–3.95(2H)<br>3.82–4.32(4H)<br>6.95–8.28(8H) |
| 4 | (106) | —CF₃ | H | =CH— | H | —C₄H₉ | —C₄H₉ | 3250<br>1660<br>1580<br>1320<br>1260<br>1020 | 0.77–1.17(6H)<br>1.17–1.93(8H)<br>3.67–3.94(2H)<br>3.87–4.20(4H)<br>6.97–8.30(8H) |
| 5 | (108) | —CF₃ | Cl | =CH— | —CH₃ | —C₂H₅ | —C₂H₅ | 3200<br>1675<br>1580<br>1320<br>1260<br>1080 | 1.10–1.55(9H)<br>3.80–4.17(4H)<br>4.50(1H)<br>6.87–8.17(7H) |
| 6 | (110) | —CF₃ | Cl | =CH— | —CH₂CH₃ | —C₂H₅ | —C₂H₅ | 3200<br>1675<br>1580<br>1320<br>1260<br>1080 | 0.97–1.40(9H)<br>1.47–2.07(2H)<br>3.80–4.50(5H)<br>6.90–8.17(7H) |
| 7 | (200) | —CF₃ | Cl | =N— | H | —C₂H₅ | —C₂H₅ | 3230<br>1660<br>1580<br>1320<br>1130<br>1070 | 1.17–1.40(6H)<br>3.67–3.90(2H)<br>3.87–4.33(4H)<br>7.27–8.27(6H) |
| 8 | (202) | —CF₃ | Cl | =N— | H | —C₄H₉ | —C₄H₉ | 3250<br>1670<br>1580<br>1320<br>1130<br>1070 | 0.80–1.13(6H)<br>1.13–1.90(8H)<br>3.80–4.03(2H)<br>4.00–4.37(4H)<br>7.30–8.33(6H) |
| 9 | (204) | —CF₃ | H | =N— | H | —C₂H₅ | —C₂H₅ | 3220<br>1670<br>1580<br>1320<br>1130<br>1070 | 1.20–1.43(6H)<br>3.70–3.93(2H)<br>3.90–4.37(4H)<br>7.00–8.43(7H) |
| 10 | (206) | —CF₃ | H | =N— | H | —C₄H₉ | —C₄H₉ | 3220<br>1670<br>1580<br>1330<br>1130<br>1080 | 0.80–1.13(6H)<br>1.13–1.83(8H)<br>3.76–3.97(2H)<br>3.93–4.30(4H)<br>7.00–8.43(7H) |
| 11 | (208) | —CF₃ | Cl | =N— | —CH₃ | —C₂H₅ | —C₂H₅ | 3200<br>1660<br>1580<br>1325<br>1250<br>1050 | 1.17–1.60(9H)<br>3.77–4.30(4H)<br>4.60(1H)<br>7.27–8.23(6H) |
| 12 | (210) | —CF₃ | Cl | =N— | —CH₂CH₃ | —C₂H₅ | —C₂H₅ | 3200<br>1660<br>1580 | 0.97–1.30(9H)<br>1.50–2.10(2H)<br>3.83–4.70(5H) |

TABLE 1-continued

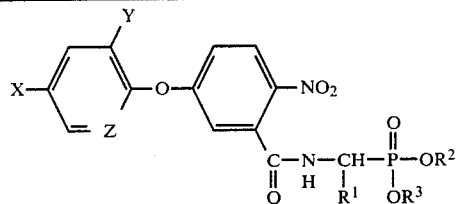

| Example | Compound No. | X | Y | Z | R¹ | R² | R³ | IR ν(cm⁻¹) | NMR in CDCl₃ δ(ppm) |
|---|---|---|---|---|---|---|---|---|---|
| | | | | | | | | 1320 1250 1050 | 7.05–8.20(6H) |

FORMULATION EXAMPLE

One part of an active compound in accordance with this invention was added to 5000 parts of a mixture of acetone and water (1:1 by volume), and 2.6 parts of a nonionic surfactant (Sorpol 2680, tradename) to form a solution.

TEST EXAMPLE 1

Active compounds in accordance with this invention were formulated in accordance with Formulation Example above.

Test plants were those obtained by sowing seeds in soil and growing them for 2 to 3 weeks after emergence.

The formulations containing the active compounds of this invention were applied in predetermined dosages, and thereafter, the plants were grown for 3 weeks without applying the formulations. The results are shown in Table 2.

TEST EXAMPLE 2

Seeds of plants were sown in soil, and on the second day after sowing, treated as follows. The growth of the plants was then observed for 3 weeks.

The formulations prepared as above were applied uniformly to the surface of the soil after sowing in predetermined dosages, and then the plants were grown without applying the formulations. The results are shown in Table 3.

TABLE 2

| Compound No. | Rate of application (g/10a) | A | B | C | D | E | F | G | H | I | J | K | L | M | N | O | P |
|---|---|---|---|---|---|---|---|---|---|---|---|---|---|---|---|---|---|
| (100) | 100 | 4 | 5 | 5 | 5 | 4 | 5 | 5 | 4 | 4 | 4 | 5 | 4 | 4 | 0 | 0 | 0 |
| (102) | 100 | 4 | 5 | 4 | 4 | 3 | 4 | 4 | 3 | 2 | 2 | 4 | 3 | 3 | 0 | 0 | 0 |
| (104) | 100 | 4 | 5 | 4 | 4 | 4 | 4 | 4 | 3 | 2 | 2 | 4 | 2 | 2 | 0 | 0 | 0 |
| (200) | 100 | 4 | 5 | 5 | 3 | 4 | 4 | 4 | 3 | 3 | 3 | 5 | 5 | 4 | 0 | 0 | 0 |
| (202) | 100 | 4 | 5 | 5 | 4 | 5 | 4 | 4 | 3 | 2 | 3 | 5 | 4 | 2 | 0 | 0 | 0 |
| (204) | 100 | 3 | 4 | 4 | 2 | 3 | 3 | 3 | 2 | 2 | 3 | 4 | 3 | 2 | 0 | 0 | 0 |
| (108) | 100 | 3 | 4 | 4 | | | 2 | | 3 | | | 5 | 4 | 2 | 0 | 0 | 0 |
| (110) | 100 | 3 | 4 | 4 | | | 2 | | 2 | | | 4 | 3 | 2 | 0 | 0 | 0 |
| (208) | 100 | 3 | 3 | 4 | | | 2 | | 2 | | | 3 | 3 | 2 | 0 | 0 | 0 |
| (210) | 100 | 3 | 3 | 4 | | | 2 | | 2 | | | 3 | 2 | 2 | 0 | 0 | 0 |

TABLE 3

| Compound No. | Rate of application (g/10a) | Q | R | K | L | M | S | T | O | P |
|---|---|---|---|---|---|---|---|---|---|---|
| (100) | 100 | 5 | 5 | 5 | 5 | 5 | 5 | 3 | 0 | 0 |
| | 50 | 5 | 5 | 3 | 3 | 3 | 2 | 2 | 0 | 0 |
| (102) | 100 | 5 | 5 | 3 | 4 | 3 | 2 | 2 | 0 | 0 |
| (200) | 100 | 5 | 5 | 5 | 5 | 5 | 4 | 5 | 0 | 0 |
| (202) | 100 | 5 | 5 | 5 | 5 | 4 | 3 | 5 | 0 | 0 |
| | 50 | 5 | 5 | 3 | 3 | 3 | 2 | 2 | 0 | 0 |
| (108) | 100 | 5 | 5 | 3 | 3 | 3 | | | 0 | 0 |
| (110) | 100 | 5 | 5 | 4 | 3 | 3 | | | 0 | 0 |
| (208) | 100 | 5 | 5 | 3 | 4 | 3 | | | 0 | 0 |
| (210) | 100 | 4 | 5 | 3 | 3 | 2 | | | 0 | 0 |

The alphabetical indications given in the column of "Plant" in Tables 2 and 3 represent the following plants.

A: *Chenopodium album L.*
B: *Amaranthus lividus Loise I.*
C: *Portulaca oleracea L.*
D: *Ambrosia artemisiaefolia L.*
E: *Datula stramonium L.*
F: *Solanum nigrum L.*
G: *Ipomoea purpurea*
H: *Desmodium tortuosum*
I: *Cirsium arvense var. setosum*
J: *Polygonum convolvulus L.*
K: *Abutilon theophrasti*
L: *Digitaria adscendens Henr.*
M: *Setaria faberi*
N: rice
O: corn
P: soybean
Q: *Amaranthus retroflexas L.*
R: *Erigeron annuus L.*
S: *Echinochloa crus-galli*
T: *Sorghum halepense*

What is claimed is:

1. A benzoylaminoalkylphosphonic compound represented by the formula

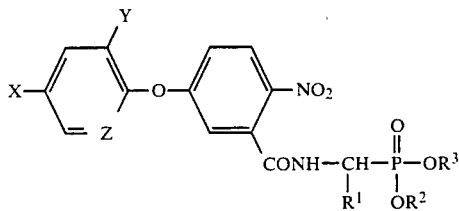

wherein X and Y are identical or different and each represents a hydrogen atom, a halogen atom, CF$_3$, or an alkyl group having not more than 5 carbon atoms, Z is CH or N, and R$^1$, R$^2$ and R$^3$ are identical or different and each represents a hydrogen atom or a lower alkyl group having 1 to 5 carbon atoms.

2. A benzoylaminoalkylphosphonic compound of claim 1 which is represented by the formula

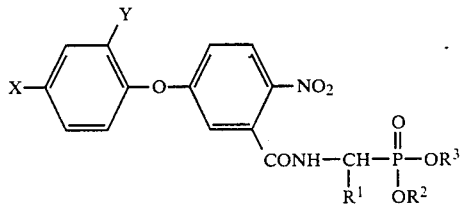

wherein X and Y are identical or different, and each represents a hydrogen atom, a halogen atom, CF$_3$, or an alkyl group having not more than 5 carbon atoms, and R$^1$, R$^2$ and R$^3$ are identical or different and each represents a hydrogen atom or a lower alkyl group having 1 to 5 carbon atoms.

3. A benzoylaminoalkylphosphonic compound of claim 1 which is represented by the formula

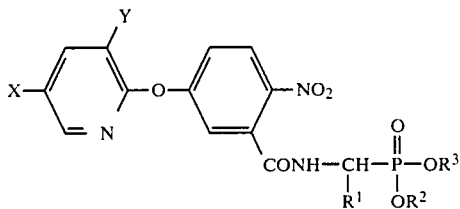

wherein X and Y are identical or different, and each represents a hydrogen atom, a halogen atom, CF$_3$, or an alkyl group having not more than 5 carbon atoms, and R$^1$, R$^2$ and R$^3$ are identical or different and each represents a hydrogen atom or a lower alkyl group having 1 to 5 carbon atoms.

4. A herbicidal composition comprising a herbicidally effective amount of a benzoylaminoalkylphosphonic compound of claim 1 as a herbicidally active ingredient in association with a herbicidally acceptable carrier.

5. A composition of claim 4 wherein the herbicidally active ingredient is a benzoylaminoalkylphosphonic compound according to claim 2.

6. A composition of claim 4 wherein the herbicidally active ingredient is a benzoylaminoalkylphosphonic compound according to claim 3.

7. A method of eradicating weeds, which comprises applying a benzoylaminoalkylphosphonic compound of claim 1 to a locus where broad-leaved weeds are growing or are likely to grow in an amount effective for eradicating the weeds.

8. A method of claim 7 wherein the locus is a locus where a crop is cultivated, and the crop is either a broad-leaved or narrow-leaved plant.

* * * * *